United States Patent
Preciado et al.

(10) Patent No.: US 12,070,269 B2
(45) Date of Patent: Aug. 27, 2024

(54) OPTICAL COHERENCE TOMOGRAPHY INSTRUMENT AND OPTICAL COHERENCE TOMOGRAPHY METHOD

(71) Applicant: OPTOS PLC, Dunfermline (GB)

(72) Inventors: Miguel Angel Preciado, Dunfermline (GB); Lijo Varughese Chacko, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 463 days.

(21) Appl. No.: 17/532,501

(22) Filed: Nov. 22, 2021

(65) Prior Publication Data

US 2022/0218196 A1    Jul. 14, 2022

(30) Foreign Application Priority Data

Jan. 13, 2021   (EP) .................................. 21 151 419
Nov. 10, 2021   (EP) .................................. 21 207 444

(51) Int. Cl.
*A61B 3/10*        (2006.01)
*G01B 9/02091*     (2022.01)

(52) U.S. Cl.
CPC .......... *A61B 3/102* (2013.01); *G01B 9/02091* (2013.01)

(58) Field of Classification Search
CPC ..... A61B 3/102; A61B 3/1225; A61B 3/0016; A61B 3/14; G01B 9/02091
See application file for complete search history.

(56) References Cited

U.S. PATENT DOCUMENTS

| | | | |
|---|---|---|---|
| 7,733,497 B2 | 6/2010 | Yun et al. | |
| 8,797,551 B2 | 8/2014 | Kulkarni et al. | |
| 2005/0018201 A1 | 1/2005 | de Boer et al. | |
| 2005/0057756 A1 | 3/2005 | Fang-Yen et al. | |
| 2006/0232783 A1 | 10/2006 | Choma et al. | |
| 2014/0293290 A1* | 10/2014 | Kulkarni | G01N 21/4795 356/479 |

FOREIGN PATENT DOCUMENTS

| | | |
|---|---|---|
| JP | 2019063044 A | 4/2019 |
| WO | 03062802 A2 | 7/2003 |

* cited by examiner

*Primary Examiner* — James C. Jones
(74) *Attorney, Agent, or Firm* — FAEGRE DRINKER BIDDLE & REATH

(57) ABSTRACT

An optical coherence tomography instrument suitable for imaging a retina is disclosed. In the instrument, an adjustable optical frequency shifter, which can be or include an acousto-optic modulator or electro-optic modulator, is arranged either (i) between a coupler and a reference optical system, (ii) in a reference optical system, (iii) between the coupler and a front-end optical system, or (iv) in a front-end optical system. The optical frequency of reference light or signal light may adjustably be increased or decreased. In operation, a subject is arranged such that its retina is in the focal depth of the front-end optical system. The increase or decrease in the optical frequency of the reference light or the sample light can be adjusted. Thereby, an interferogram representing a depth structure at the retina obtained between returning signal light and returning reference light may be brought to lie within a detection bandwidth of the instrument.

15 Claims, 10 Drawing Sheets

OPTICAL COHERENCE TOMOGRAPHY INSTRUMENT AND OPTICAL COHERENCE TOMOGRAPHY METHOD

This application claims the benefit of priority based on European Patent Application EP 21 151 419.5 filed Jan. 13, 2021 and European Patent Application EP 21 207 444.7 filed Nov. 10, 2021, each of which is incorporated by reference herein in its entirety, as if set forth fully herein.

FIELD

Example aspects herein relate to an optical coherence tomography, and, more particularly, to an optical coherence tomography instrument and method for performing an optical coherence tomography measurement of a retina.

BACKGROUND

Optical coherence tomography (OCT) is an imaging technique capable of obtaining high-resolution measurements and imaging of surface and subsurface structures of, by example and without limitation, human tissue, particularly the retina, non-invasively.

In optical coherence tomography, measurement light is split into two paths by an optical coupler. The optical coupler directs light in each path to a different arm of an interferometer. One arm is termed a reference arm, while the other is termed a sample arm. In the sample arm, the light is directed by a sample optical system, sometimes termed a front-end optical system, to a sample under investigation, and reflected light is collected by the sample optical system and returned to the optical coupler. In the reference arm, the light enters a reference optical system which returns the light to the optical coupler. The returning light from the sample arm and the reference arm are recombined by the coupler to generate an interference pattern. The interference pattern is recorded by a detector.

The interference pattern contains information about the optical path travelled by the reflected sample light and the magnitude of the sample light having travelled a particular optical path length. Since the wavelength of the light is selected to at least partially penetrate the sample under investigation, the interference pattern contains information about surface and subsurface structures of the sample.

Different implementations of the optical coherence tomography technique are known in the art. One technique, termed swept-source optical coherence tomography (SS-OCT), uses measurement light, the optical frequency of which is periodically modulated in a controlled way across a defined source bandwidth. Typically, a series of rising sweeps over a defined optical frequency band are used as the modulation. A temporally-varying interference pattern signal is recorded by the detector. A Fourier transform of the recorded signal over one periodic modulation of the optical frequency of the measurement light generates an axial depth profile of the sample, with intensity corresponding to a strength of the reflection.

Scanning the measurement light one- or two-dimensionally across the surface of the sample enables an axial depth profile to be obtained for each of a plurality of points across the surface of the sample such that a two- or three-dimensional depth profile of the sample can be obtained.

A coherence length of the measurement light determines the imaging depth of the system, while the source bandwidth determines an axial resolution of the system. Moreover, an optical path length of the reference arm determines an axial position at which the axial depth profile is obtained.

Conventionally, the optical path length of the reference arm is either fixed or is mechanically adjustable by, for example, a movable mirror to place an axial region from which an axial depth profile may be measured at or around the surface of the sample. However, fixing the optical path length of the reference arm results in an inflexible system, while mechanical adjustment of the optical path length of the reference arm is insufficiently fast, reliable or precise.

It would be useful to provide an optical coherence tomography instrument and method that enable fast, reliable and precise adjustment of the axial position around which the axial depth profile can be obtained.

SUMMARY

According to an example aspect herein, there is provided an optical coherence tomography instrument for imaging a retina. The instrument comprises an optical coupler arranged to accept light from a tuneable narrowband light source and to split the light into at least signal light and reference light. The instrument also comprises a reference optical system arranged to return the reference light, and a front-end optical system arranged to direct the signal light towards an eye of a subject and to return reflected signal light from the eye of the subject. The instrument also comprises a detection unit arranged to sample a time-varying interference signal between the returned reference light and the returned signal light. An adjustable optical frequency shifter is arranged either (i) between the coupler and the reference optical system, (ii) in the reference optical system, (iii) between the coupler and the front-end optical system, or (iv) in the front-end optical system. The adjustable optical frequency shifter is arranged to adjustably increase or decrease the optical frequency of the reference light or the signal light.

In one example embodiment herein, the reference optical system comprises a reflector arranged to reflect the reference light to return the reference light.

Also in an example embodiment herein, the reflector is fixed relative to the coupler.

Further, according to an example embodiment herein, the reference optical system comprises an optical loop to return the reference light. The optical loop can have a fixed optical path length, although this example is not limiting.

According to an example embodiment herein, the reference light passes by way of the optical frequency shifter in forward and reverse directions.

According to a further example embodiment herein, the signal light passes by way of the optical frequency shifter in forward and reverse directions.

The optical frequency shifter includes an acousto-optic modulator or electro-optic modulator, in one example embodiment herein.

In still another example embodiment herein, the instrument further comprises a radio frequency driver arranged to drive the acousto-optic modulator or electro-optic modulator to obtain a predetermined optical frequency shift.

Also in accordance with an example embodiment herein, the optical coupler includes a beam splitter or a fibre coupler.

The instrument further can comprise the tuneable narrowband light source, wherein the tuneable narrowband light source is arranged to emit the narrowband light to the coupler.

In one example embodiment herein, the narrowband light has a coherence length of greater than 0.5 cm, optionally greater than 1 cm, optionally greater than 10 cm.

The tuneable narrowband light source comprises a tuneable vertical cavity surface emitting laser, in one example embodiment herein, although that example is not limiting.

The tuneable narrowband light source is configured to periodically vary an optical frequency of the light emitted thereby, according to an example embodiment herein.

Also, according to an example embodiment herein, the detector comprises one of a photodetector or a balanced photodetector.

According to another example aspect herein, there is provided an optical coherence tomography method. The method comprises arranging a subject such that a retina of the subject is in a focal depth of a front-end optical system of an optical coherence tomography instrument. The method comprises introducing narrowband light having periodically varying optical frequency into a coupler to cause the coupler to split the light into at least signal light and reference light, wherein the reference light is reflected back by a reference optical system, and the signal light is reflected back by an eye of the subject. The method also comprises recording a time-varying interference signal between the reflected reference light and the reflected signal light, the recording being based on a detection of the time-varying interference signal by a detection unit having a detection bandwidth defined by a sample frequency of the detection unit. The method further comprises adjusting the optical frequency of the reference light or the signal light. The adjusting, according to one example embodiment herein, is performed such that an interferogram representing a depth structure at the retina obtained between reflected signal light and the reflected reference light lies within the detection bandwidth.

BRIEF DESCRIPTION OF THE DRAWINGS

For a better understanding of the present disclosure, and to show how the same may be put into effect, reference will be made to the accompanying drawings, now described as follows.

DETAILED DESCRIPTION

Figure 1:
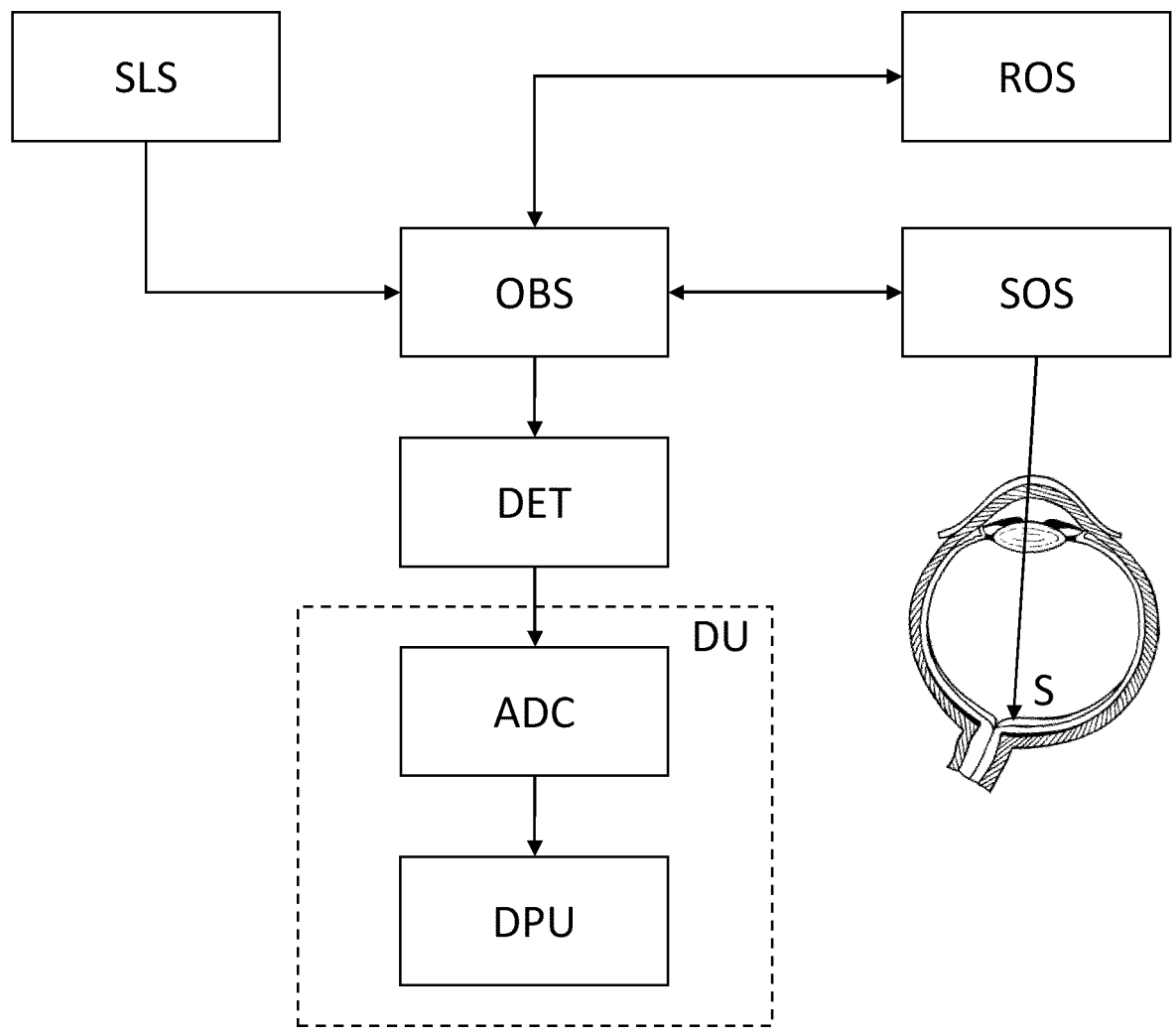
FIG. 1 is a schematic diagram of an optical coherence tomography instrument (system) according to example embodiment herein.

FIG. 1 is a schematic diagram of an optical coherence tomography instrument (also referred to herein as an optical coherence tomography system) constructed according to an example embodiment herein.

Figure 2:
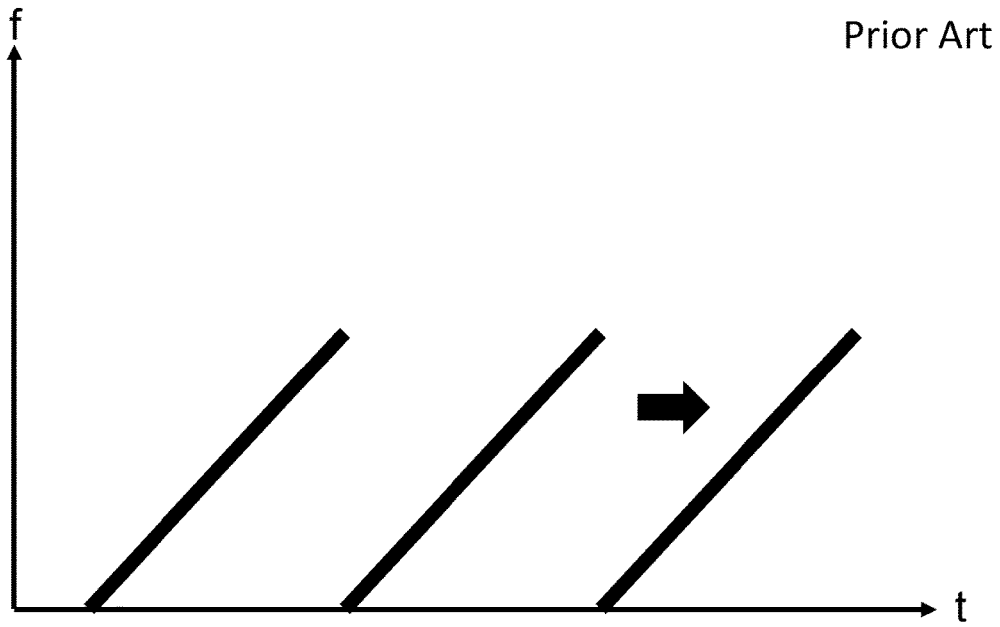
FIG. 2 is a graphical representation of a periodic frequency sweep provided by a swept source typical of optical coherence tomography instruments.

In the instrument of FIG. 1, a swept light source SLS generates a beam of narrowband light with a variable centre frequency. Swept light source SLS is configured to vary the centre frequency of the narrowband light in a repetitive manner, such as by a repeated periodic frequency sweep over a defined frequency band between a lower frequency and an upper frequency. Such a periodic frequency sweep is exemplified in FIG. 2, which shows the frequency of an output of such a swept light source SLS with respect to time. Such a frequency sweep is conventionally termed a chirp. The sweep may rise in time from low frequency to high frequency, or may fall in time from high frequency to low frequency. The sweep may also successively rise and fall in time. For example, a forward sweep from low to high frequency may be followed by a reverse sweep from high to low frequency. The seep range may be of the order of, for example, 100 nm. Swept light source SLS may have high coherence, and for example may have a coherence length in excess of 5 mm. In some configurations, the coherence length may exceed 10 mm, or may even exceed 100 mm. Of course, these examples are non-limiting.

In one example embodiment herein, the swept light source SLS is a tuneable laser or a tuneable laser diode, and includes, for example, an external cavity laser, an optical parametric amplifier, a Fourier-domain mode-locking laser (FDML) or a tuneable vertical cavity surface-emitting laser (VCSEL), although these examples are not limiting to the scope of the invention. The bandwidth of swept light source SLS, in one example embodiment herein, can be selected for optimum penetration through, for example, a lens of an eye under examination and tissues of a retina of the eye. Also in an example embodiment herein, the bandwidth is in the infra-red region of the optical spectrum, for example, at wavelengths longer than 850 nm. Example wavelengths which may be included in the sweep are 850 nm, 1050 nm, 1310 nm or 1550 nm, although these examples are not limiting.

The beam of narrowband light generated by swept light source SLS is directed to optical beam splitter OBS which acts as an optical coupler to split the beam of narrowband light from light source SLS into two beams. The splitting of the beam may be symmetric, such that equal intensity is directed into the resulting two beams, or may be asymmetric, such that unequal intensity is directed into the resulting two beams.

A first beam, also referred to herein as a sample beam, is directed to a sample optical system SOS, which includes optical components to shape and direct the light beam to a sample S, such as, by example only, a retina, and to collect reflected light (i.e., light reflected from the sample S) and return it to the optical beam splitter OBS. The reflected light follows essentially the same path to the optical beam splitter OBS as the sample beam, but in a reverse direction.

In one example embodiment herein, the sample optical system SOS includes conventional components known in the field of optical coherence tomography, and, in some example embodiments herein, such conventional components are adapted according to the imaging operation to be performed. More particularly, in one example embodiment herein the sample optical system SOS can include scanning optics which can cause a pivoting of the sample beam about a pivot point located in an anterior segment of the eye (e.g., sample S) in order to scan the sample beam across a wide field of the retina located in a posterior segment of the eye.

As one example, the sample optical system SOS may include one or more scanners arranged to scan the beam in one or more directions across the retina. Such scanners can include oscillating plane mirrors such as galvanometer scanners, MEMS mirrors, rotating mirrors, prism or polygon scanners or resonant scanners.

The sample optical system may also include a scan relay unit comprising, for example, a lens or curved mirror, arranged to image one scanner which scans the beam in one direction onto a subsequent second scanner which scans the beam in a second direction, thereby to generate a two-dimensional scan pattern arising from an apparent origin located at the second scanner.

The sample optical system may also include a scan transfer unit, for example, a lens or curved mirror, arranged to project the apparent origin into space beyond the sample optical system SOS, so that the two-dimensional scan pattern arising from the apparent origin at the second scanner is transferred to an apparent pivot point in the space beyond the sample optical system, such that the sample beam pivots about the pivot point in the scan.

A second beam, also referred to herein as a reference beam, is directed to a reference optical system ROS, which then returns the reference beam to the optical beam splitter OBS. At the optical beam splitter OBS, the returning reflected light (i.e., the light reflected from the sample S) and the returning reference beam (i.e., the reference beam returned from the reference optical system ROS) are combined so as to interfere with one another and are directed as interfering beams to detector DET. Detector DET, which, in one example embodiment herein, is a photodetector such as a photodiode or an avalanche photodiode, converts an optical intensity of the interfering beams to provide a resulting converted signal in the form of, e.g., an electrical signal such as a voltage or current. In one example embodiment herein, the resulting converted signal is a time-varying analogue signal. After being output by the detector DET, the resulting converted signal can be recorded in a time-varying manner, as will be described below, wherein a recorded version of the signal constitutes an interferogram between the returning reflected light and the returning reference beam with respect to the optical frequency of the narrowband light from the swept light source SLS.

In the example embodiment depicted in FIG. 1, an analogue to digital converter ADC periodically samples and quantizes the signal output by the detector DET with a predetermined sample frequency, and then digital values of the quantised and sampled signal are provided to a data processing unit DPU wherein the values are recorded. Accordingly, the detector DET and analogue to digital converter ADC together constitute a detection unit DU which samples a time-varying interference signal between the returning reference light and the returning signal light. With respect to the data processing unit DPU, in one example embodiment herein the data processing unit DPU performs a Fourier transform operation, such as a fast Fourier transform, on the time-varying quantised and sampled signal values obtained from analogue to digital converter ADC to generate an axial depth profile.

As a result of the periodic sampling of the output of detector DET by analogue to digital converter ADC, the highest-frequency components of the time-varying analogue signal, which lie outside a detection bandwidth defined by the sample frequency of the analogue digital converter ADC, are not recorded. Simply stated, the beat frequency of these components of the interferogram are too high to be recorded. For example, the highest-frequency components of the time-varying analogue signal may be greater than the Nyquist frequency of the analogue digital converter, and conversely the sample rate may be less than the Nyquist rate of the highest-frequency components of the interferogram.

The swept light source SLS may have relatively high coherence length such that the interference between the returning reflected light and the returning reference beam contains information about the reflectivity of the sample over a large axial depth range defined by the high coherence length. Nonetheless, only information about a sub-range of this axial depth range corresponding to the detection bandwidth, centred on an axial position defined by the optical path length of the reference arm, is available from a Fourier transform of the sampled signal recorded at the data processing unit DPU.

In conventional optical coherence tomography instruments, the optical path length of the reference arm is adjusted to set an axial position of the measured axial depth range to correspond to the position of the surface of the sample under investigation, in view of the typically low coherence length of the light source used. Thereby, an optical delay is introduced between the sample light and the reference light, which ensures that the sample light and the reference light maintain coherence when combined to interfere at the detector.

Figure 4:
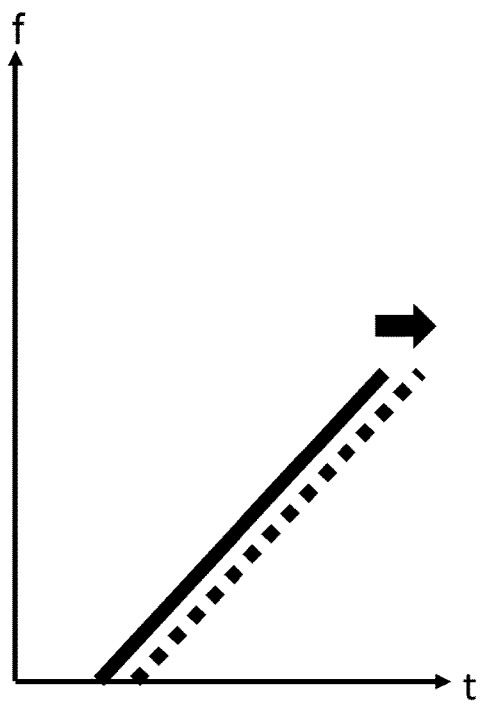
FIG. 4 shows an effect of introducing an optical delay to the periodic frequency sweep of FIG. 2 by means of an increased optical path length.
Figure 3:
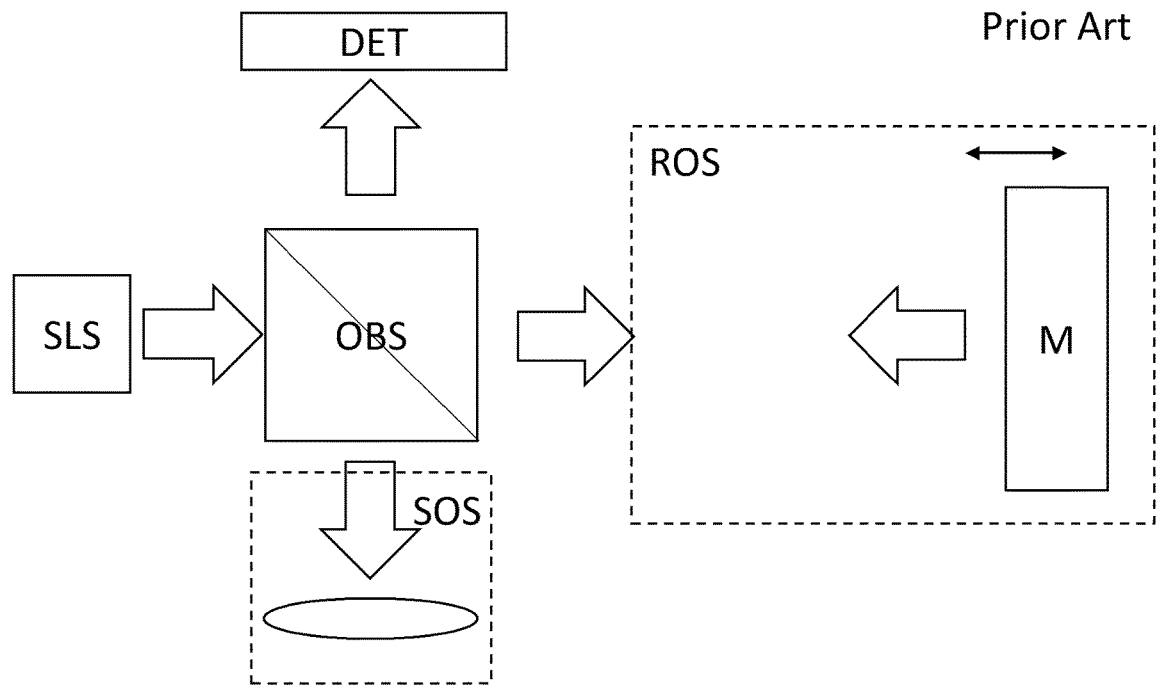
FIG. 3 shows at least part of a conventional optical coherence tomography instrument (system) including, among other components, a reference arm and a sample arm.

An exemplary configuration of such an arrangement is shown in FIG. 3, in which a movable mirror M is provided in the reference optical system ROS to alter the optical path length travelled by light in the reference arm. Such an alteration to the optical path length travelled by light in the reference arm corresponds to a variable optical delay of the frequency chirp generated by the swept light source SLS as shown in FIG. 4. In the present configuration, an optical delay is introduced to the reference light; it should be understood that the optical delay is relative to the sample light and may in principle be positive or negative depending on whether the optical path of the sample arm is greater or smaller in length than the optical path of the reference arm.

The present inventors have recognised that when the swept light source SLS has sufficiently high coherence, a constant frequency shift, such as a frequency upshift or downshift, applied to the frequency chirp generated by the swept light source SLS, corresponds substantially to a constant optical delay, with the amount of equivalent delay introduced corresponding to the amount of frequency shift introduced.

Figure 6:
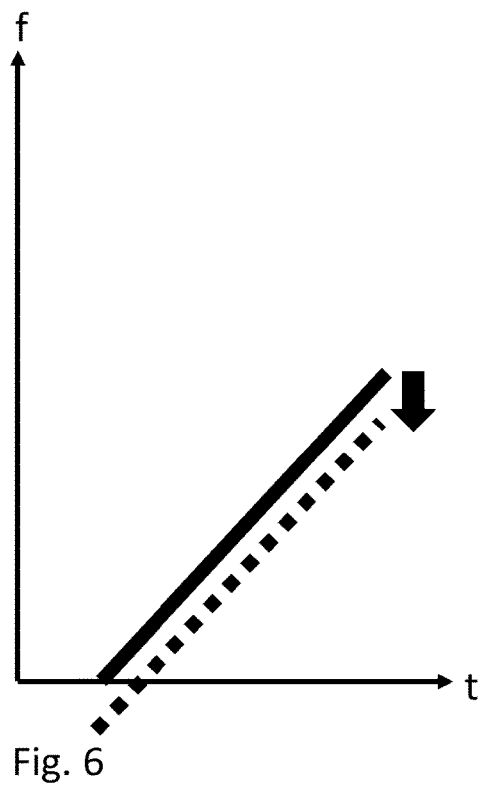
FIG. 6 shows an effect of introducing an optical frequency downshift to the periodic frequency sweep of FIG. 2 by means of an optical frequency shifter.
Figure 5:
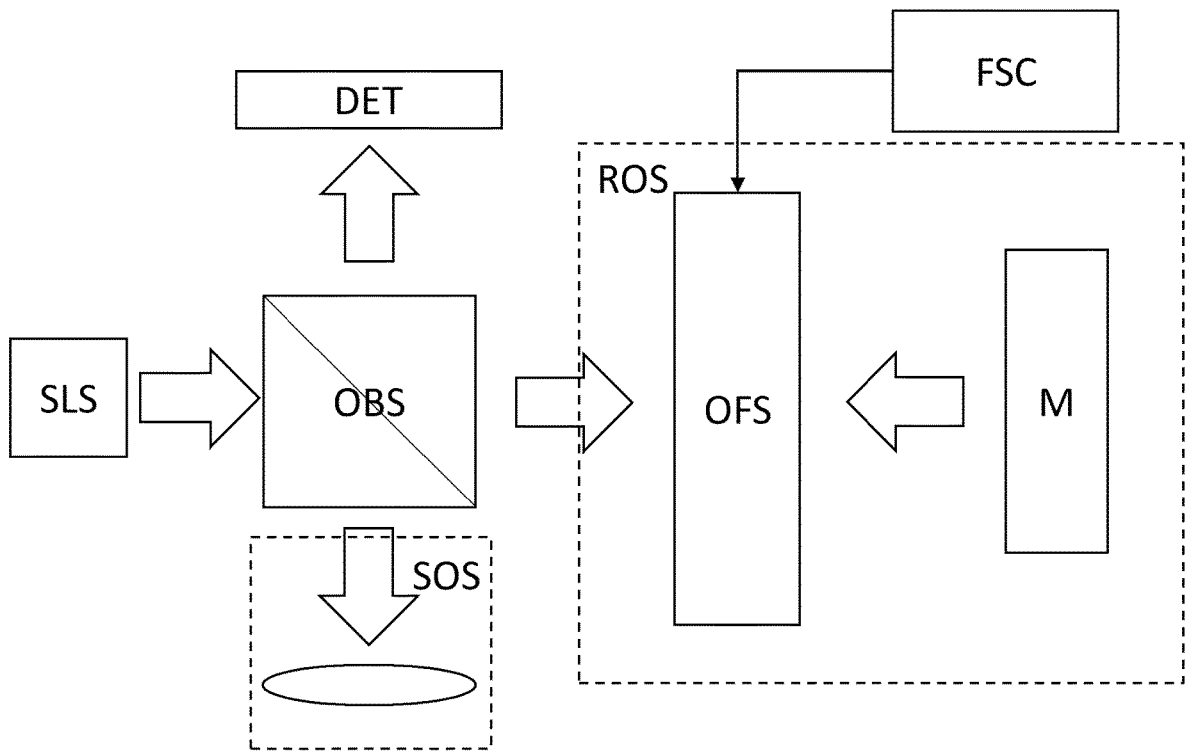
FIG. 5 shows an optical coherence tomography instrument (system) according to an example embodiment herein, including, among other components, reference and sample arms.
Figure 16:
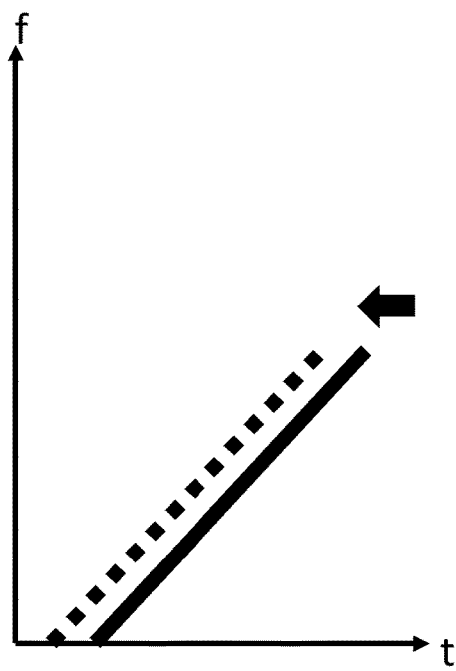
FIG. 16 shows an effect of introducing a reverse optical delay to the periodic frequency sweep of FIG. 2 by means of an increased optical path length.
Figure 17:
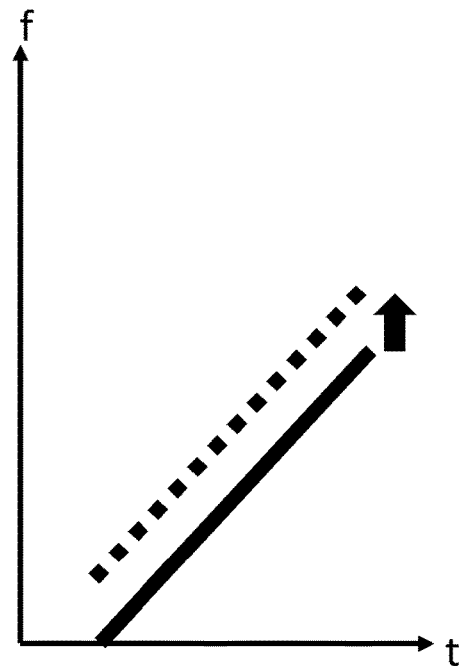
FIG. 17 shows an effect of introducing an optical frequency upshift to the periodic frequency sweep of FIG. 2 by means of an optical frequency shifter.

According to an example aspect herein, such a frequency shift may be introduced by placing an optical frequency shifter OFS into the reference arm, for example in the reference optical system ROS, between the optical beam splitter OBS and the mirror M as shown in FIG. 5. The effect on the frequency chirp generated by the swept light source SLS is shown in FIG. 6, from which it can be seen, by comparison with FIG. 4, that the introduction of a predetermined frequency shift is equivalent to the introduction of a predetermined optical delay. Whereas FIGS. 4 and 6 show the effect of introducing a frequency downshift, a frequency upshift is also contemplated FIGS. 16 and 17 correspond to FIGS. 4 and 6 for the case of a frequency upshift.

Figure 13:
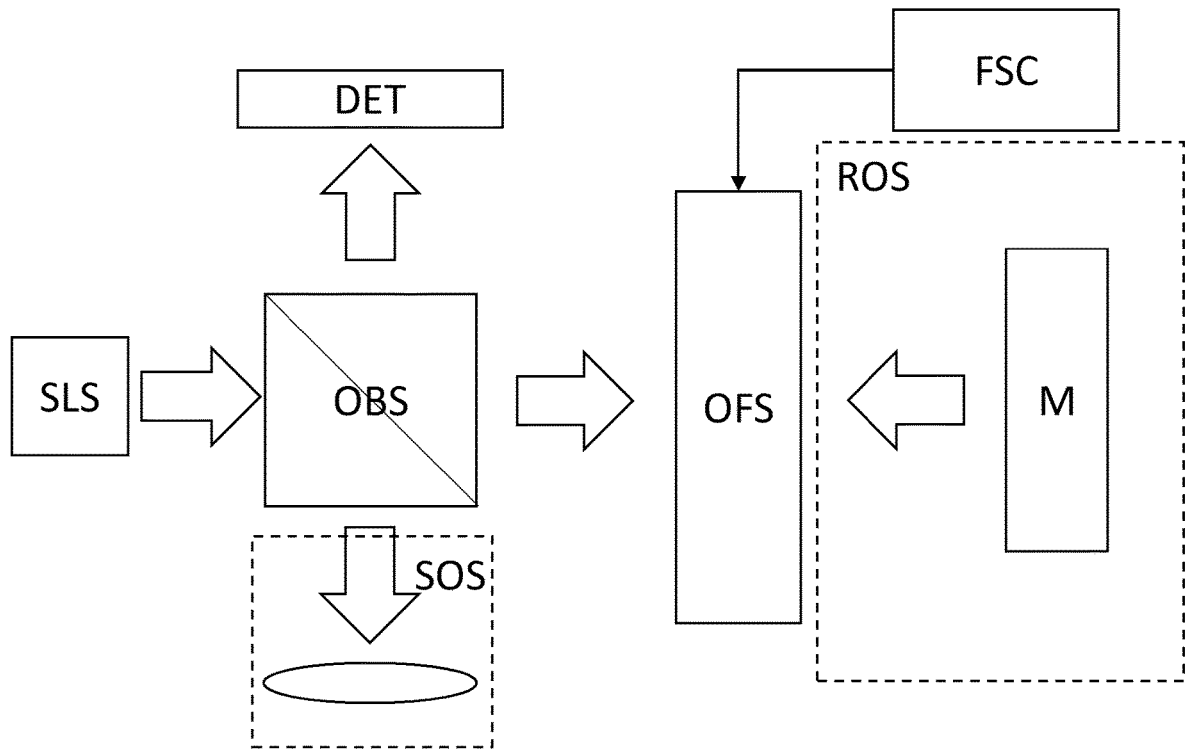
FIG. 13 shows an optical coherence tomography instrument (system) according to an example embodiment herein, in which an optical frequency shifter is arranged between an optical beam splitter and a reference optical system.
Figure 14:
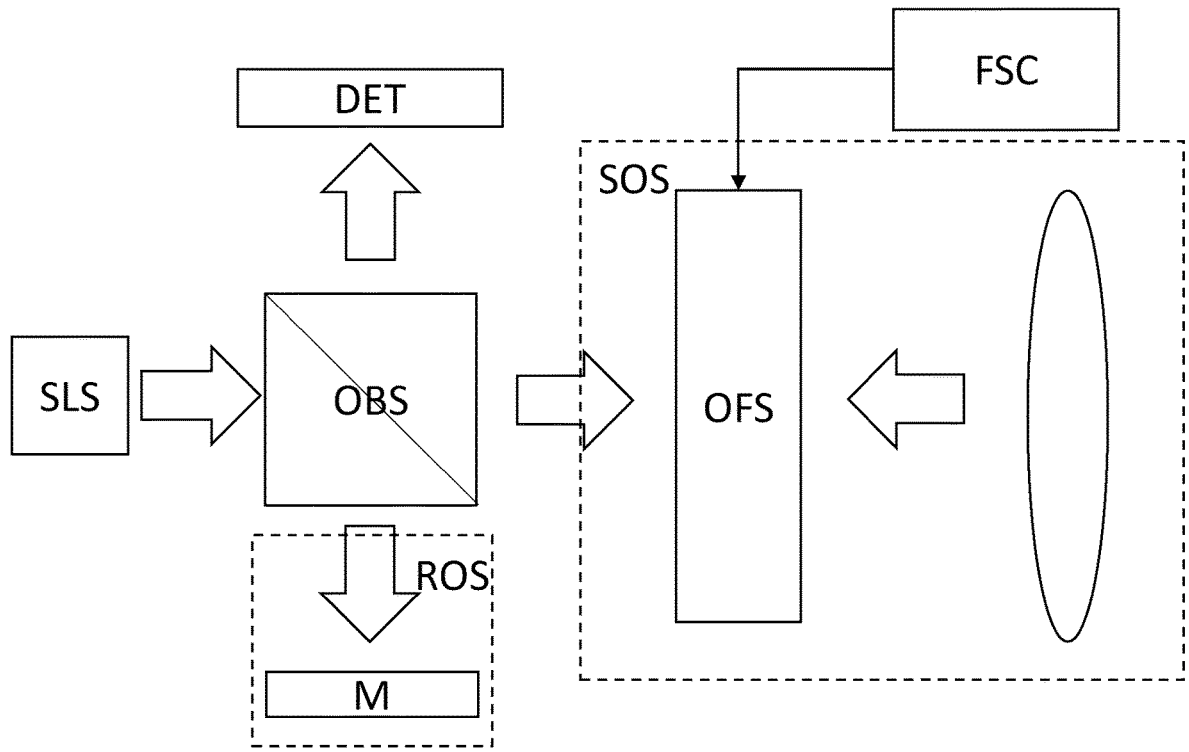
FIG. 14 shows an optical coherence tomography instrument (system) according to an example embodiment herein, in which an optical frequency shifter is in a sample optical system.
Figure 15:
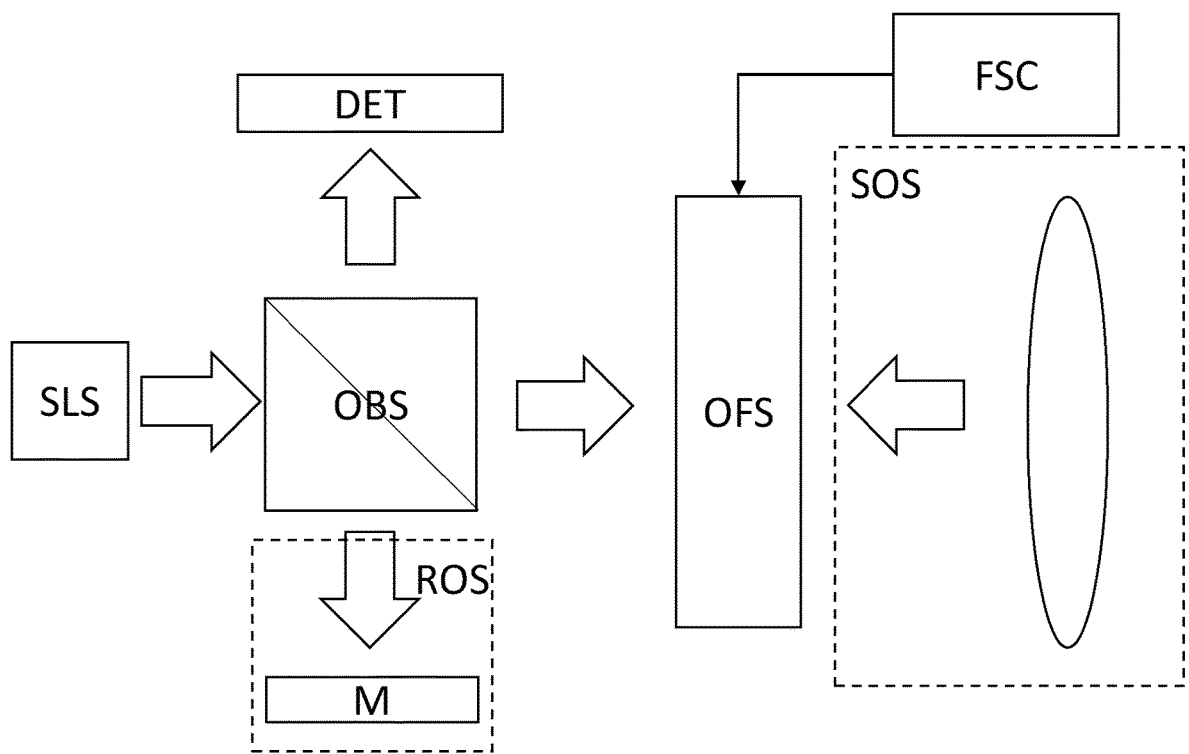
FIG. 15 shows an optical coherence tomography instrument (system) according to an example embodiment herein, in which an optical frequency shifter is arranged between an optical beam splitter and a sample optical system.

Equivalently, the optical frequency shifter may be arranged between the optical beam splitter OBS and the reference optical system ROS, as shown in FIG. 13. Similarly, by placing an optical frequency shifter OFS into the sample optical system SOS, a frequency shift may be introduced to the sample arm which would correspond to an optical delay in the sample arm. Such a configuration is shown in FIG. 14. Equivalently, the optical frequency shifter may be arranged between the optical beam splitter OBS and the sample optical system SOS, as shown in FIG. 15.

The optical frequency shifter OFS is controllable by a frequency shift controller FSC. By virtue of the frequency shift controller FSC controlling the optical frequency shifter OFS to adjust the amount of frequency shift introduced, an effect equivalent to introducing an adjustable optical delay by means of, for example, a movable mirror M as shown in FIG. 3, can be achieved, without using any moving parts. Accordingly, by introducing a predetermined amount of frequency upshift or downshift to the light in the sample arm or reference arm, the temporal interference frequency between the returning reflected light of the sample beam and the returning light of the reference beam can be slowed so that interference components arising from a desired axial region of the sample lie within the available detector bandwidth defined by the sample frequency. Stated simply, the beat frequency of the interferogram components arising from the desired axial region of the sample S is slowed sufficiently to enable it to be recorded. Consequently, the electrical frequency of the electrical signal output by the detector is also reduced. As one example, the frequency of the interferogram components arising from the desired axial region of the sample may be reduced to lower than the Nyquist frequency of the analogue-digital converter.

As optical frequency shifter OFS, an acousto-optic modulator (AOM) may be used to introduce the optical frequency shift, according to one example embodiment herein.

An acousto-optic modulator comprises a driven optical medium to which vibrations are applied at a defined frequency. The vibrations induce phonons in the optical medium which interact with photons passing through the optical medium to generate diffracted light having a frequency shift proportional to the frequency of the vibration, with the constant of proportionality determined by the order of diffraction. Accordingly, by varying the frequency of the vibration, a well-defined optical frequency shift may be introduced. Depending on the order of diffraction, and particularly whether the diffractive order is a positive or negative order, the optical frequency shift is either an upshift or downshift. Such acousto-optic modulators can operate in a travelling-wave configuration or a standing wave configuration. In such a configuration, the frequency shift controller FSC is a radio-frequency driver arranged to apply a variable radio-frequency electric signal to the optical medium using a piezo-electric element attached to the optical medium.

As optical frequency shifter OFS, an electro-optic modulator (EOM) may alternatively be used to introduce the optical frequency shift, according to one example embodiment herein.

An electro-optic modulator comprises an optical medium exhibiting an electro-optical effect to which an electric field is applied. The electric field may be applied to the medium, for example, by placing the medium between the plates of a parallel-plate capacitor. The applied electric field induces a corresponding change in the refractive index of the optical medium according to the strength of the electric field, due to the electro-optic effect. Without wishing to be bound by theory, such change in refractive index may typically be caused by forces that distort the position, orientation, or shape of the molecules constituting the optical medium. The change in refractive index induces a change in the phase of the light exiting the medium. If the electric field is varied with a defined frequency, the refractive index varies also with that defined frequency. The varying of the refractive index may induce a correspondingly varying change in the phase of the light exiting the optical medium.

For example, if the electric field is varied sinusoidally at a predetermined frequency ω, then a time-dependent phase at the predetermined frequency ω may be added to the time dependence of the electromagnetic wave of the light, for example of frequency Ω exiting the optical medium. As a result of the addition of this time-dependent phase, a set of sidebands comprising at least a first pair of sidebands are added to the light at frequencies at frequency Ω±ω, each sideband of the first pair of sidebands shifted in frequency by the predetermined frequency co relative to the frequency Ω of the light. Accordingly, by varying the frequency of the electric field, a well-defined optical frequency shift may be introduced to the light. Due to the presence of two sidebands, an optical frequency shift which is an upshift or downshift can be obtained.

In another example embodiment, the electro-optic modulator (EOM) may alternatively be used to introduce the optical frequency shift by means of amplitude modulation, rather than phase modulation.

In particular, a phase-modulating electro-optic modulator can be used to introduce amplitude modulation to an incident light by incorporating at least one such electro-optic modulator into a corresponding at least one arm of an interferometer, such as a Mach-Zehnder interferometer, to which the incident light is applied. Such an interferometer has having two arms, into which the incident light is coherently separated, and which generate output light by coherently combining the light of the two arms. The coherent separation and combining of the light can be performed by one or more beam-splitters. This arrangement is sometimes termed a Mach-Zehnder modulator (MZM). In related arrangements, one electro-optic modulator can be provided to each of two arms of the interferometer.

Applying an electric field across the optical medium of the electro-optic modulator in the interferometer introduces a phase shift according to the strength of the electric field, as described above. Depending on the introduced phase shift, the amplitude of the light output from the interferometer will also vary according to the amount of phase shift introduced, in accordance with the normal principles of an interferometer. Thereby, a varying amplitude can be imparted to the light. The magnitude of the variation of the applied electric field may be set such that the difference in introduced phase shift between minimum and maximum applied electric field corresponds to half a wavelength of the input light. In such a configuration, a variation in the applied electric field at a predetermined frequency $\omega$ results in a variation in the amplitude of the output light also with a predetermined frequency $\omega$ For example, if the electric field is varied sinusoidally at a predetermined frequency $\omega$, then a time-dependent amplitude at the predetermined frequency $\omega$ may be added to the time dependence of the electromagnetic wave of the light, for example of frequency $\Omega$ exiting the optical medium. As a result of the addition of this time-dependent amplitude, a set of sidebands comprising only a first pair of sidebands are added to the light at frequencies at frequency $\Omega \pm \omega$, each sideband of the sidebands shifted in frequency by the predetermined frequency $\omega$ relative to the frequency $\Omega$ of the light. Accordingly, by varying the frequency of the electric field, a well-defined optical frequency shift may be introduced to the light. Due to the presence of two sidebands, an optical frequency shift which is an upshift or downshift can be obtained.

When sidebands are generated as frequency-shifted light, for example through the use of an electro-optic modulator or Mach-Zehnder modulator, it may be necessary to select only the sideband light for further use. Selecting the upper sideband light can be performed by incorporating, for example, a suitable high-pass filter after the interferometer or modulator, whereas selecting the lower sideband light can be performed by incorporating, for example, a suitable low-pass filter after the modulator. However, where the sidebands are sufficiently different in frequency from the incident light, then it may not be needed to include a filter. For example, by using an electro-optic modulator or Mach-Zehnder modulator, a frequency offset of several gigahertz can be achieved for the shifted light compared with the input light. In such a situation, a filter may be omitted.

In such a configuration, the frequency shift controller FSC is a radio-frequency (which may include microwave frequency) driver arranged to apply a variable radio-frequency or microwave frequency electric signal to the optical medium using a suitable pair of capacitor plates attached to or arranged adjacent the optical medium, thereby to apply the variable electric field across the optical medium.

As the medium for an electro-optic modulator, lithium niobite ($LiNbO_3$) may be used. Other media may be used, including nonlinear or birefringent media. Example alternative media include potassium di-deuterium phosphate (KD*P or DKDP), potassium titanyl phosphate (KTP), beta-barium borate (BBO), lithium tantalate ($LiTaO_3$) and ammonium dihydrogen phosphate ($NH_4H_2PO_4$ or ADP). In addition to these inorganic media, nonlinear polymer media such as poled polymers may be used as the medium.

In other example embodiments herein, other nonlinear optical techniques can be used to produce the desired frequency upshift or downshift. For example, difference-frequency generation or half-harmonic generation using, for example, a nonlinear optical crystal may be used instead of the acousto-optic modulator or electro-optic modulator to introduce a desired frequency shift.

In accordance with an example aspect herein, a function of the optical frequency shift is to bring high-frequency interference components within the lower-frequency detection bandwidth. This can be achieved by an optical frequency shift which is an upshift or a downshift, depending on the direction of sweep of the laser, whether the frequency shift is applied in the reference arm or the sample arm.

For example, if the frequency shifter is incorporated into the reference arm, for a swept source which sweeps from low frequency to high frequency, a downshift introduced to the reference arm may be appropriate. Also, if the frequency shifter is incorporated into the reference arm, for a swept source which sweeps from high frequency to low frequency, an upshift introduced to the reference arm may be appropriate. If, on the other hand, the frequency shifter is incorporated into the sample arm, for a swept source which sweeps from low frequency to high frequency, a downshift introduced to the sample arm may be appropriate. Moreover, if the frequency shifter is incorporated into the sample arm, for a swept source which sweeps from high frequency to low frequency, an upshift introduced to the sample arm may be appropriate. Hence, a particular frequency shifter can be used to introduce both positive or negative delay. However, the effect of a positive or negative delay can increase or decrease the beating frequency of the interference, depending on whether this introduced delay causes the reference and sample arms to move relatively more in or out of phase.

A piezo-electric transducer can be used to apply vibrations to a driven optical medium, wherein the piezo-electric transducer itself is driven by a radio-frequency (RF) voltage applied across the transducer. Accordingly, in one example embodiment herein, the optical frequency shifter OFS represented in FIG. 5 can be or include an acousto-optic modulator or electro-optic modulator, for example as part of a Mach-Zehnder modulator, driven by a variable-frequency RF signal generated by frequency shift controller FSC. Thus, the sample frequency, and thus detector bandwidth, remains constant while the amount of frequency shift may be adjusted to reduce the beat frequency of the interferogram and to bring the region of interest of the interferogram within the detector bandwidth.

Referring again to FIG. 5, the reference light can travel twice through optical frequency shifter OFS, in particular, in one instance in the forward direction from optical beam splitter OBS to mirror M by way of the optical frequency shifter OFS, and in another instance in the reverse direction from mirror M optical beam splitter OBS by way of the optical frequency shifter OFS. On each pass through the optical frequency shifter OFS, the predetermined frequency shift associated with the driving frequency supplied by frequency shift controller FSC is introduced. Hence, in the example configuration of FIG. 5, the total shift applied is twice the frequency shift introduced by the optical frequency shifter OFS for each individual pass.

In the above descriptions of the example configurations of FIG. 5, the effect of optical frequency shifter OFS has been explained in connection with a free-space optic arrangement of the optical coherence tomography instrument. However, that arrangement is not limiting to the scope of the invention. Indeed, in other example embodiments herein, optical-fibre-based configurations can be employed in which optical fibres are used in place of free space to propagate beams of light.

Figure 7:
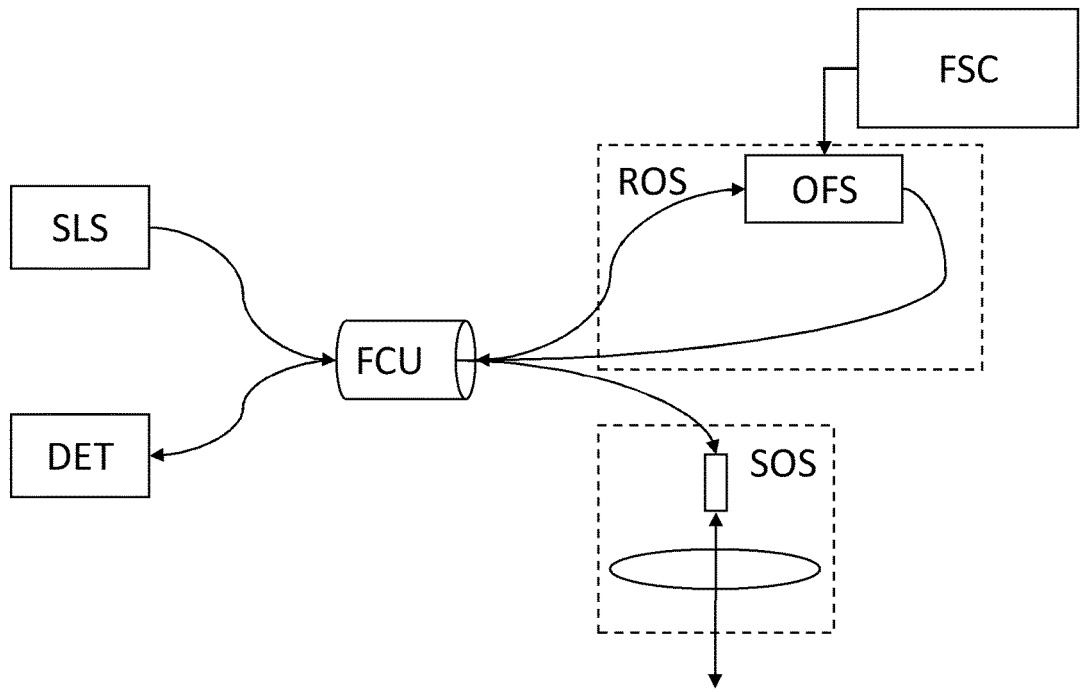
FIG. 7 shows an optical coherence tomography instrument according to another example embodiment herein, including, among other components, reference and sample arms.

For example, FIG. 7 shows another example embodiment herein of an optical coherence tomography instrument (also referred to herein as an "optical coherence tomography system"). In FIG. 7, light from swept light source SLS travels via an optical fibre to a fibre coupler unit FCU which provides the function of the optical coupler. The light from swept light source SLS thereby splits into a reference beam and a sample beam (also referred to as "sample light"). The reference beam is forwarded in a reference arm, circulates via optical frequency shifter OFS controlled by a frequency shift controller FSC, and returns to fibre coupler unit FCU. The sample light is forwarded in a sample arm and travels via sample optical system SOS to sample S (not shown in FIG. 7), which reflects the sample light so it returns to fibre coupler unit FCU by way of sample optical system SOS. At the fibre coupler unit FCU, the returning light received from each arm is combined and passed along a further optical fibre to detector DET. Otherwise, the embodiment of FIG. 7 operates in the same way as the that of FIG. 3, except that, since the light in the reference arm passes through the optical frequency shifter OFS only once, only a single, rather than a double, frequency shift is applied.

Figure 8:
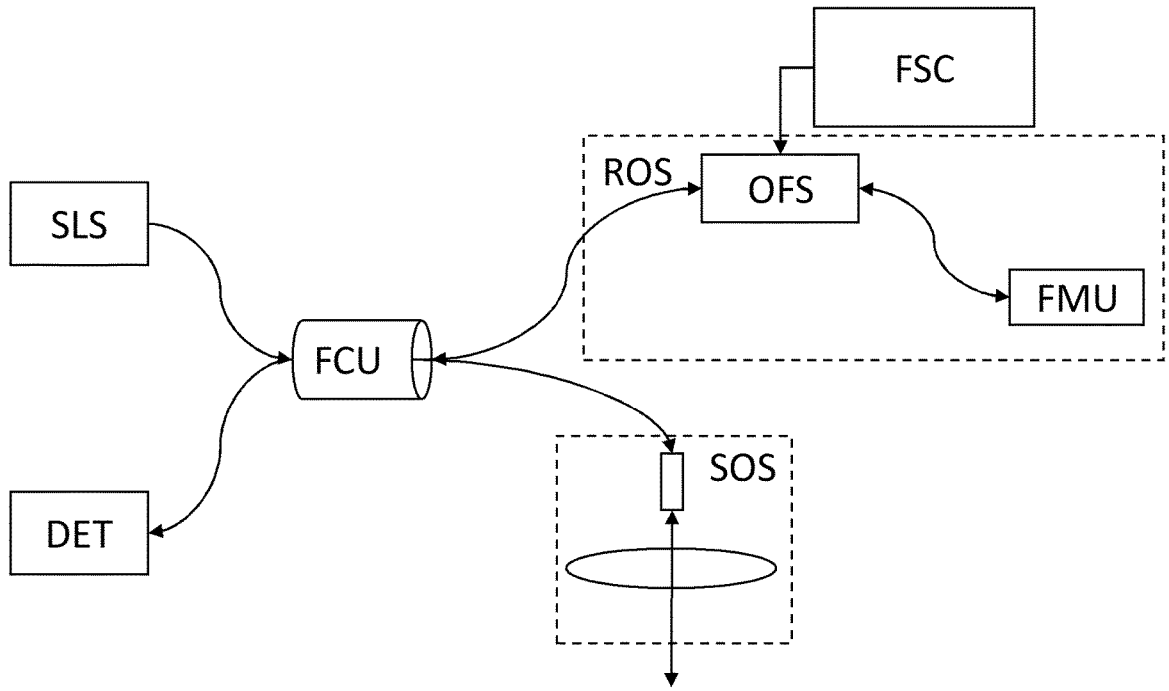
FIG. 8 shows an optical coherence tomography instrument according to still another example embodiment herein.

A further example embodiment of an optical coherence tomography instrument is illustrated in FIG. 8. The instrument of FIG. 8 includes the same components as those of FIG. 7, except that the reference optical system ROS of the embodiment of FIG. 8 differs from that of the embodiment of FIG. 7. In FIG. 8, the reference beam traveling in the reference arm is provided, by way of optical frequency shifter OFS, to a fibre mirror unit FMU. The fibre mirror unit FMU reflects incident light received from optical frequency shifter OFS and returns reflected light via the optical frequency shifter OFS to the fibre coupler unit FCU. Thereby, a double frequency shift is introduced in the same manner as in the free-space optical arrangement of FIG. 5.

In one example embodiment herein, the embodiments of FIGS. 1, 5, 7 and 8 are implemented using so-called unbalanced detection, in which the interfering frequency components are directly detected from an optical signal of detector DET. However, in other example embodiments herein a balanced detection arrangement can be employed instead in which the signal and reference arms are independently coupled to different optical inputs of detector DET, such that the signal and reference light are combined to interfere at or in detector DET through an optical or electrical medium. In such an arrangement, the intensity of the signal and reference light may also independently be measured, for example, by diverting at least some of each of the sample and reference light to a separate detection element, such that variations in the intensity of light can be compensated by the detection elements.

Figure 9:
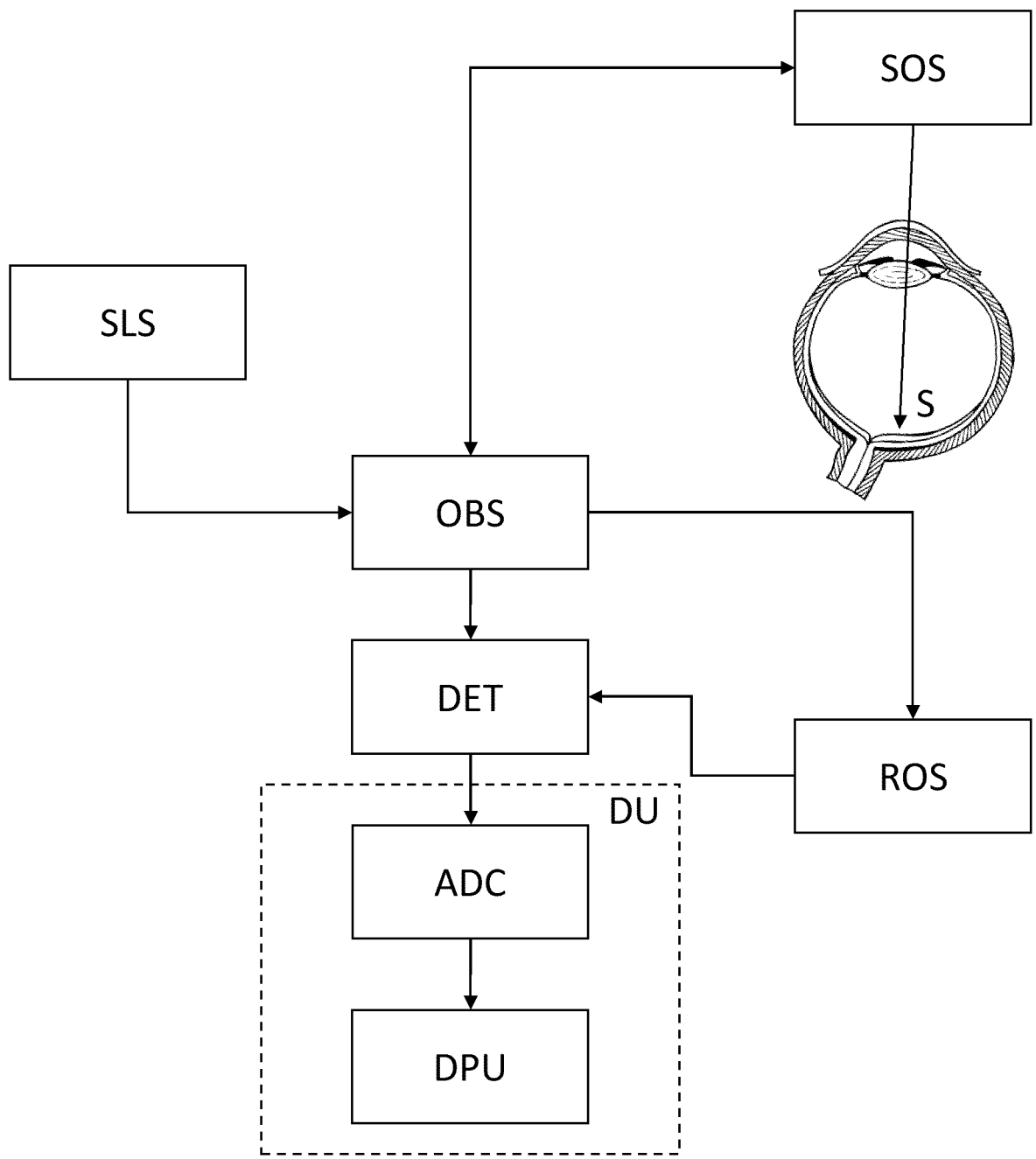
FIG. 9 is a schematic diagram of an optical coherence tomography instrument using balanced detection, according to still a further example embodiment herein.

FIG. 9 illustrates an example embodiment herein of an optical coherence tomography instrument employing balance detection. The instrument of FIG. 9 is similar to that of FIG. 1, except that in the instrument of FIG. 9 the detector DET comprises two optical inputs, and the reference optical system ROS is included in a loop optical system between an output of optical beam splitter OBS and one of the two optical inputs of detector DET. The loop optical system comprises the optical beam splitter OBS, the reference optical system ROS, and the detector DET. In one example embodiment herein, the optical loop has a fixed optical path length, although this example is not limiting. The interference between the returning reference and sample light in the detector provides the interferogram.

Figure 10:
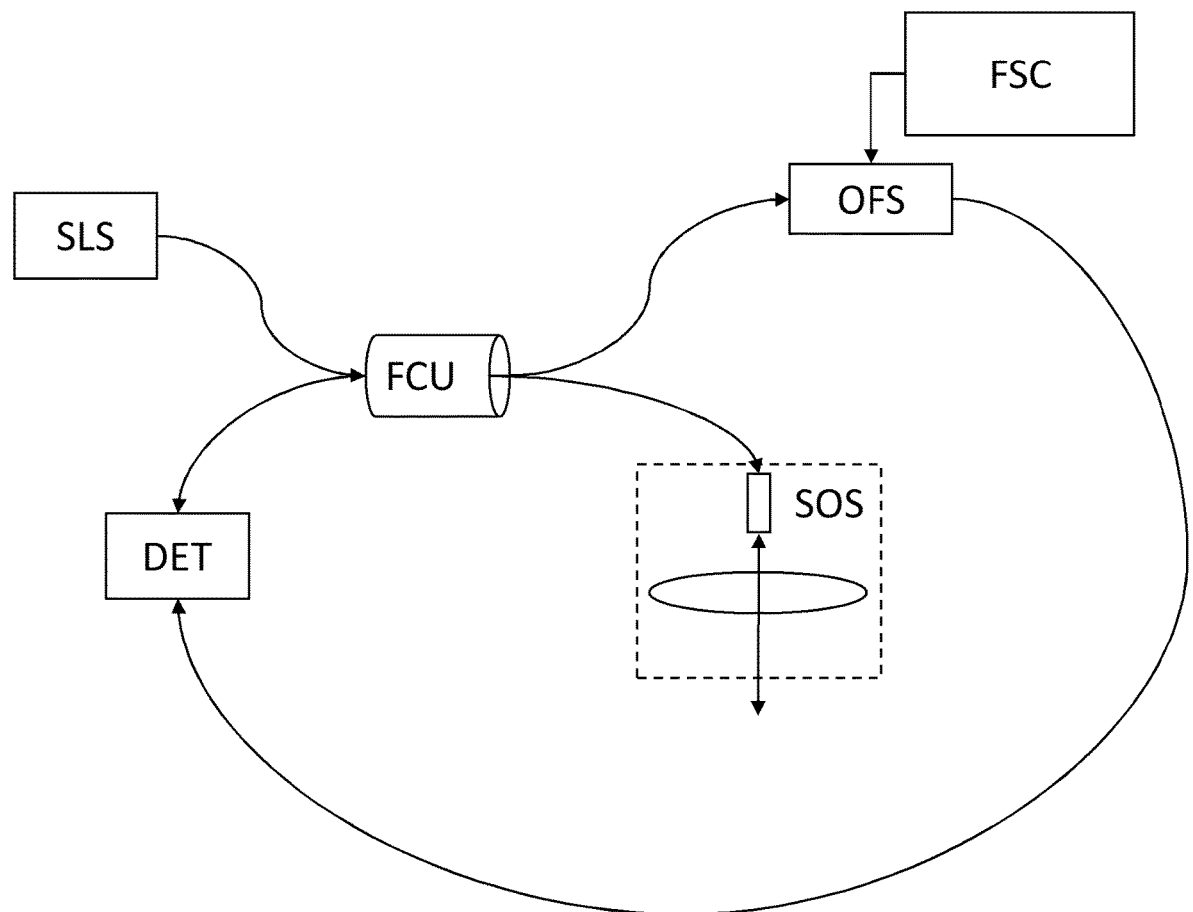
FIG. 10 shows another optical coherence tomography instrument using balanced detection, according to another example embodiment herein.

FIG. 10 illustrates another example embodiment herein of an optical coherence tomography instrument, wherein the instrument has an optical fibre configuration. The instrument of FIG. 10 includes similar components as the instrument of FIG. 7, except that the reference optical system ROS is not represented in FIG. 10 and, instead of an output of the optical frequency shifter OFS being provided to the fibre coupler unit FCU as represented in FIG. 7, in the instrument of FIG. 10 the output of the optical frequency shifter OFS is provided a first one of plural inputs of detector DET. Accordingly, an optical fibre loop is provided that includes fibre coupler unit FCU, optical frequency shifter OFS, and detector DET. As such, a reference beam output by the fibre coupler unit FCU is provided to optical frequency shifter OFS, and an output of optical frequency shifter OFS is provided to the first input of the detector DET. A second input of detector DET receives returning sample light which returns from sample optical system SOS through fibre coupler unit FCU. The interference between the returning reference and sample light in the detector provides the interferogram.

The above configurations have been described in relation to discrete control and data processing units, such as the internal controller of swept light source SLS, the frequency shift controller FSC controlling optical frequency shifter OFS and the data processing unit DPU transforming the detected optical signal of detector DET into an axial depth profile using a fast Fourier transform. However, in other example embodiments herein, at least some or all of the control and data processing aspects of the above configurations may be provided by an integrated controller which may be instantiated as a programmable logic unit (PLU), application-specific integrated circuit (ASIC), a supervisory control and data acquisition system (SCADA), a general purpose data processor such as a microcomputer, minicomputer, or personal computer (PC), or a mobile device such as a tablet computer or smartphone.

Figure 11:
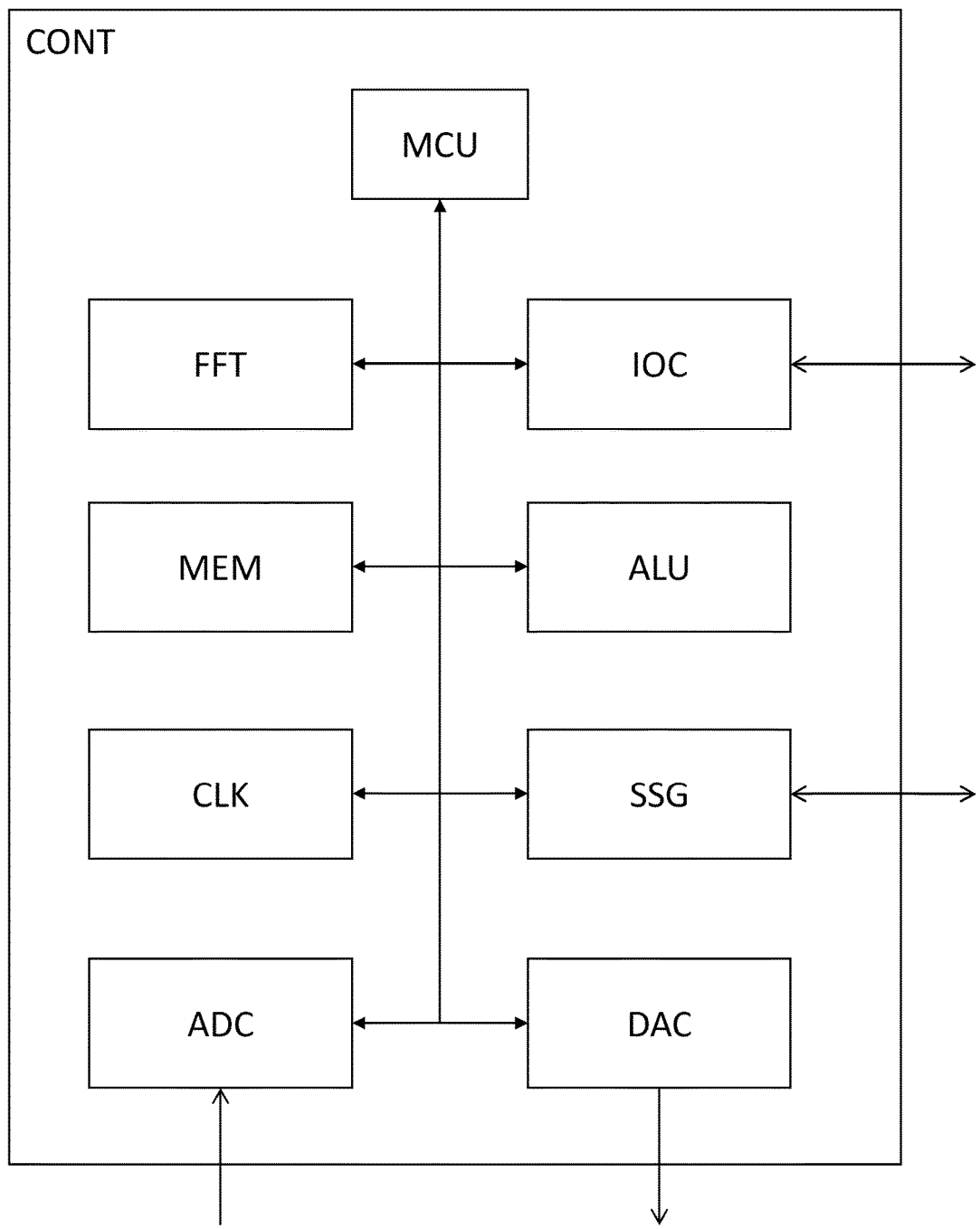
FIG. 11 is a schematic diagram of a controller for controlling an optical coherence tomography instrument, according to an example embodiment herein.

A schematic diagram of an example embodiment herein of an integrated controller CONT is shown in FIG. 11. In one example embodiment herein, the integrated controller CONT controls at least some or all of the various components shown in FIGS. 1, 3, 5, and 7-10, and also may form all or at least part of the frequency shift controller FSC. As represented in FIG. 11, all of the components of the integrated controller CONT are coupled to one another and thus can inter-communicate. Integrated controller CONT shown in FIG. 11 comprises an analogue to digital converter ADC to receive, quantize and sample signals from a detector DET (not shown in FIG. 11), and, in one example embodiment herein, provide resulting converted signals to one or more other components of integrated controller CONT, such as, by example only, master control unit MCU. In one example embodiment herein, integrated controller CONT also comprises a digital to analogue converter that converts digital signals received from one or more other components of the integrated controller CONT, such as, by example only, the master control unit MCU, to analogue value(s) and provides them as analogue control voltage(s) to a frequency shift controller FSC (not shown in FIG. 11), to thereby define an amount of frequency shift introduced by optical frequency shifter OFS (not shown in FIG. 11). Integrated controller CONT also comprises a sweep signal generator SSG which outputs a time varying signal for control of frequency of a swept light source SLS (not shown in FIG. 11). For example, the output of sweep signal generator SSG may be a time-varying voltage, and swept light source SLS may accept a voltage input to define the centre frequency of the output narrowband light. Integrated controller CONT also comprises a clock generator CLK which defines one or more clocks for providing a common time base for the operation of time-varying aspects of the controller CONT. For example, clock generator CLK may define a sample clock for analogue to digital converter ADC as well as a time base for sweep signal generator SSG. Clock generator CLK may also define internal clocks of controller CONT such as memory and instruction clocks and data bus clocks. Integrated controller CONT also comprises a fast Fourier transform unit FFT to perform Fourier transform on quantised and sample signals obtained via analogue to digital converter ADC. Integrated control unit also comprises an arithmetic and logic unit ALU for performing arithmetical logical operations on data handled within indicated controller CONT.

Integrated controller CONT also comprises a memory MEM, which in one example embodiment herein is computer-readable, for storing and retrieving data values such as recorded data from analogue to digital converter ADC, signal waveforms associated with sweep signal generator SSG, Fourier-transformed output data generated by fast Fourier transform unit FFT, and other parameters, instructions and values as necessary for performing the operations of integrated controller CONT. The memory MEM may comprise, by example only and without limitation, a RAM, ROM, hard drive, floppy disc, memory stick, a buffer, or the like. In one example embodiment herein, the memory MEM stores instructions and/or programs for performing the methods and functions described herein and represented in the drawings. Integrated controller CONT also comprises an input output controller IOC for sending and receiving values to external devices such as off-line storage instantiated as a hard drive, flash drive or disk drive, or an interface such as a network interface, for example a wired local area network, a wireless area network, or a mobile data network. Integrated controller also comprises a master control unit MCU which coordinates operations of the various functional units of controller CONT, and thus controls the other components of integrated controller CONT. In one example embodiment herein, the master control unit MCU (and/or the arithmetic and logic unit ALU) can read and write data, instructions and programs from/to the memory MEM, and can execute the instructions and programs to perform the methods and functions described herein and represented in the drawings. Also in an example embodiment herein, the analogue to digital converter ADC of FIG. 11 may form and/or be included in the analogue to digital converter ADC of the other figures described herein, and the master control unit MCU and/or the integrated controller CONT may form and/or be included in the frequency shift controller FSC and/or the digital processing unit DPU of the other figures described herein. However, the division of various functional tasks into units as shown in FIG. 11 is purely exemplary, and such tasks may be performed by individual functional modules, discrete electronics, integrated logic, other hardware, software and/or other program code, as required.

Figure 12:
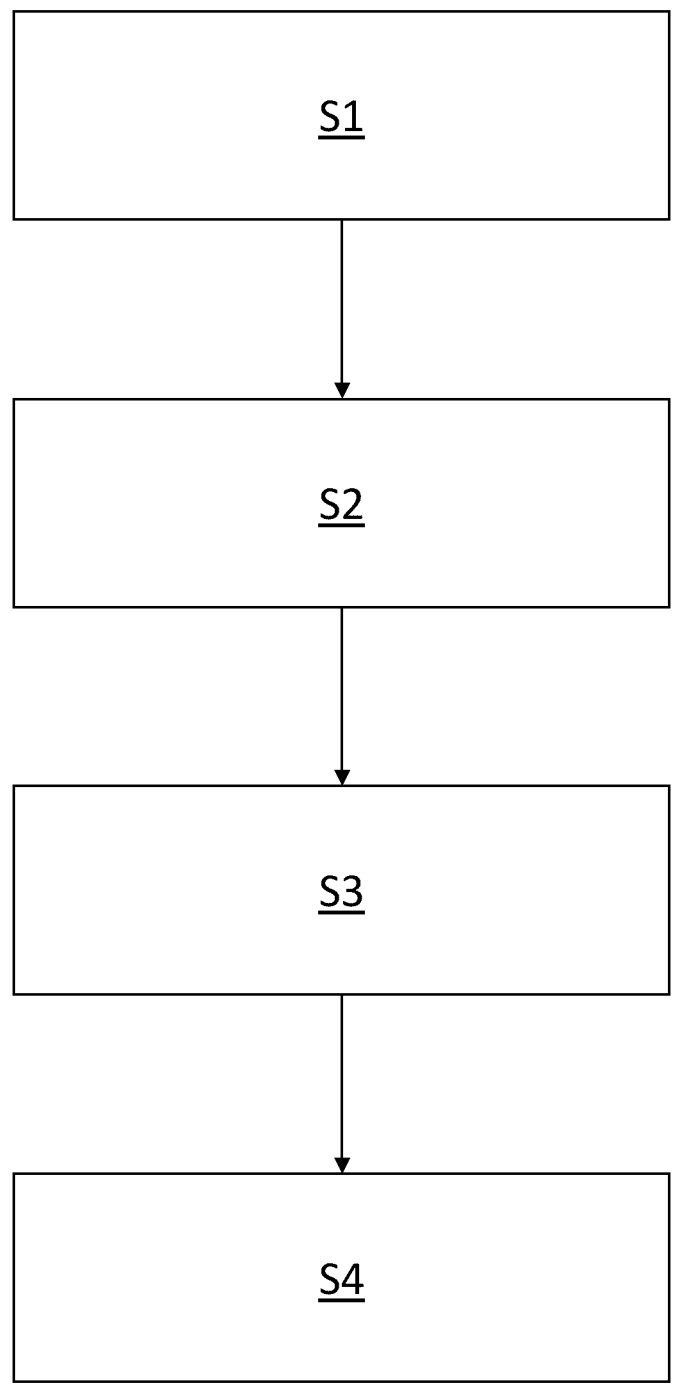
FIG. 12 is a flow diagram illustrating an optical coherence tomography method according to an example embodiment herein.

FIG. 12 illustrates an optical coherence tomography method which according to an example embodiment herein, wherein the method can be implemented by one or more individual ones of the optical coherence tomography instruments described above and shown in the drawings. In step S1, a sample (e.g., sample S) such as the retina of a subject is arranged in a focal depth of a front-end optical system (e.g., sample optical system SOS) of the optical coherence tomography instrument.

In step S2, narrowband light of light having a periodically varying optical frequency is introduced into an optical coupler (e.g., fibre coupler unit FCU) to be split between a sample arm and a reference arm. In the sample arm, sample light is directed via the front-end optical system to illuminate the retina. Returning reflected light is captured by the front-end optical system and returned to the optical coupler via the sample arm. Meanwhile, reference light in the reference arm is returned to interfere with the returning light in the sample arm.

In step S3, a time-varying interference signal between the returning reference light and returning reflected light is recorded with or based on a detector (e.g., detector DET). The detector is characterised by a detection bandwidth defined by a sample frequency of the detector. The time-varying interference signal recorded with the detector is subjected to a Fourier transform to generate an axial depth profile.

In step S4, an optical frequency shift is introduced/applied by the optical frequency shifter (e.g., optical frequency shifter OFS) to light in the sample or reference arm, depending on predetermined operating criteria. The optical frequency shift is adjusted, for example by decrease of the frequency as shown in FIG. 6, to vary the optical frequency of the light passing through the optical frequency shifter. The amount of optical frequency shift is adjusted until the interferogram between light reflected from the retina and the reference light lies within the detection bandwidth.

Thereby, an axial depth profile can be obtained in a manner as described above, wherein the axial depth profile obtained represents depth structure at the retina. Notably, the axial depth profile is obtained substantially without necessarily requiring moving any parts of the sample or reference arms. This can be determined by observing the axial depth profile, or can be detected programmatically by, for example, detecting a signal characteristic of the retinal surface structure in the axial depth profile.

The disclosed apparatus and methods may be implemented in a scanning laser ophthalmoscope (SLO), according to one example embodiment herein. Alternatively, the disclosed apparatus and methods may be implemented to measure tissue other than the retina, and other than tissue of the eye. For example, the disclosed apparatus and methods may be implemented to measure other biological membranes such as skin or plant parts, or may be applied to measure non-biological structures.

It should be noted that, although for convenience the analogue to digital converter ADC and digital processing unit DPU are not represented in FIGS. 5, 7, 8, and 10, it will be readily understood by one skilled in the art in view of this description that the instruments (systems) of those figures also can include those components, wherein in such a configuration, for example, the digital processing unit DPU is coupled to the detector DET of those respective instruments by way of the converter ADC interposed therebetween.

In the foregoing description, example aspects are described with reference to several example arrangements. Accordingly, the specification should be regarded as illustrative, rather than restrictive. Similarly, the figures illustrated in the drawings, which highlight the functionality and advantages of the example arrangements, are presented for example purposes only. The architecture of the example arrangements is sufficiently flexible and configurable, such that it may be utilized in ways other than those shown in the accompanying figures.

Software arrangements of the examples presented herein may be provided as a computer program, or software, such as one or more programs having instructions or sequences of instructions, included or stored in an article of manufacture such as a memory, machine-accessible or machine-readable medium, an instruction store, or computer-readable storage device, each of which can be non-transitory, in one example arrangement. The program or instructions on the non-transitory memory, machine-accessible medium, machine-readable medium, instruction store, or computer-readable storage device, may be used to program a computer system or other electronic device. The memory, machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "memory", "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, digital processing unit, or computer processor and that causes the machine/computer/unit/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some arrangements may also be implemented by the preparation of application-specific integrated circuits, field-programmable gate arrays, or by interconnecting an appropriate network of conventional component circuits.

Some arrangements include a computer program product. The computer program product may be a memory, storage medium or media, instruction store(s), or storage device(s), having instructions stored thereon or therein which can be used to control, or cause, a computer or computer processor to perform any of the procedures of the example arrangements described herein. The memory/storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the memory, computer-readable medium or media, instruction store(s), or storage device(s), some implementations include software for controlling both the hardware of the system and for enabling the system or microprocessor to interact with a human user or other mechanism utilizing the results of the example arrangements described herein. Such software may include without limitation device drivers, operating systems, and user applications. Ultimately, such memories, computer-readable media or storage device(s) further include software for performing example aspects of the disclosure, as described above.

Included in the programming and/or software of the system are software modules for implementing the procedures described herein. In some example arrangements herein, a module includes software, although in other example arrangements herein, a module includes hardware, or a combination of hardware and software.

While various example arrangements of the present disclosure have been described above, it should be understood that they have been presented by way of example, and not limitation. It will be apparent to persons skilled in the relevant art(s) that various changes in form and detail can be made therein. Thus, the present disclosure should not be limited by any of the above described example arrangements, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example arrangements presented herein in any way. It is also to be understood that any procedures recited in the claims need not be performed in the order presented.

While this specification contains many specific arrangement details, these should not be construed as limitations on the scope of any disclosures or of what may be claimed, but rather as descriptions of features specific to particular arrangements described herein. Certain features that are described in this specification in the context of separate arrangements can also be implemented in combination in a single arrangement. Conversely, various features that are described in the context of a single arrangement can also be implemented in multiple arrangements separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the arrangements described above should not be understood as requiring such separation in all arrangements, and it should be understood that the described program components and systems can generally be integrated together in a single software product or packaged into multiple software products.

Having now described some illustrative arrangements and arrangements, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one arrangement are not intended to be excluded from a similar role in other arrangements or arrangements.

The apparatuses and methods described herein may be embodied in other specific forms without departing from the characteristics thereof. The foregoing arrangements are illustrative rather than limiting of the described systems and methods.

Scope of the apparatuses and methods described herein is thus indicated by the appended claims, rather than the foregoing description, and changes that come within the meaning and range of equivalence of the claims are embraced therein.

The invention claimed is:

1. An optical coherence tomography instrument comprising:
    an optical coupler arranged to accept light from a tuneable narrowband light source and to split the light into at least signal light and reference light;
    a reference optical system arranged to return the reference light;

a front-end optical system arranged to direct the signal light towards an eye of a subject and to return signal light reflected from the eye of the subject;

a detection unit arranged to sample a time-varying interference signal between the returned reference light and the returned signal light; and an adjustable optical frequency shifter arranged either (i) between the coupler and the reference optical system, (ii) in the reference optical system, (iii) between the coupler and the front-end optical system, or (iv) in the front-end optical system, the adjustable optical frequency shifter arranged to adjustably increase or decrease an optical frequency of the reference light or the signal light.

2. The optical coherence tomography instrument according to claim 1, wherein the reference optical system comprises a reflector arranged to reflect the reference light to return the reference light.

3. The optical coherence tomography instrument according to claim 2, wherein the reflector is fixed relative to the coupler.

4. The optical coherence tomography instrument according to claim 1, wherein the reference optical system comprises an optical loop to return the reference light, the optical loop optionally having a fixed optical path length.

5. The optical coherence tomography instrument according to claim 1, wherein the reference light passes by way of the adjustable optical frequency shifter in forward and reverse directions.

6. The optical coherence tomography instrument according to claim 1, wherein the signal light passes by way of the optical frequency shifter in forward and reverse directions.

7. The optical coherence tomography instrument according to claim 1, wherein the optical frequency shifter includes an acousto-optic modulator or an electro-optic modulator.

8. The optical coherence tomography instrument according to claim 7, further comprising a radio frequency driver arranged to drive the acousto-optic modulator or electro-optic modulator to obtain a predetermined optical frequency shift.

9. The optical coherence tomography instrument according to claim 1, wherein the optical coupler includes a beam splitter or a fibre coupler.

10. The optical coherence tomography instrument according to claim 1, further comprising the tuneable narrowband light source, wherein the tuneable narrowband light source is arranged to emit the light to the optical coupler, and the light is narrowband light.

11. The optical coherence tomography instrument according to claim 10, wherein the narrowband light has a coherence length of greater than one of 0.5 cm, 1 cm, or 10 cm.

12. The optical coherence tomography instrument according to claim 10, wherein the tuneable narrowband light source comprises a tuneable vertical cavity surface emitting laser.

13. The optical coherence tomography instrument according to any one of claim 10, wherein the tuneable narrowband light source is configured to periodically vary an optical frequency of the light emitted thereby.

14. The optical coherence tomography instrument according to claim 1, wherein the detection unit includes one of a photodetector or a balanced photodetector.

15. An optical coherence tomography method comprising:

arranging a subject such that a retina of the subject is in a focal depth of a front-end optical system of an optical coherence tomography instrument;

introducing narrowband light having a periodically varying optical frequency into a coupler to cause the coupler to split the light into at least signal light and reference light, wherein the reference light is reflected back by a reference optical system, and the signal light is reflected back by an eye of the subject;

recording a time-varying interference signal between the reflected reference light and the reflected signal light, the recording being based on a detection of the time-varying interference signal by a detection unit having a detection bandwidth defined by a sample frequency of the detection unit;

adjusting the optical frequency of the reference light or the sample light, wherein the adjusting is performed such that an interferogram representing a depth structure at the retina obtained between the reflected signal light and the reflected reference light lies within the detection bandwidth.

* * * * *